United States Patent
Jacobsen et al.

[11] Patent Number: 6,017,319
[45] Date of Patent: *Jan. 25, 2000

[54] HYBRID TUBULAR GUIDE WIRE FOR CATHETERS

[75] Inventors: Stephen C. Jacobsen; Clark Davis; John Lippert, all of Salt Lake City, Utah

[73] Assignee: Precision Vascular Systems, Inc., Salt Lake City, Utah

[ * ] Notice: This patent issued on a continued prosecution application filed under 37 CFR 1.53(d), and is subject to the twenty year patent term provisions of 35 U.S.C. 154(a)(2).

[21] Appl. No.: 08/653,289

[22] Filed: May 24, 1996

[51] Int. Cl.⁷ .................................................. A01B 5/00
[52] U.S. Cl. ........................... 600/585; 604/96; 604/281
[58] Field of Search .................. 128/772, 657, 128/658; 604/95, 96, 210, 281, 282, 283

[56] References Cited

U.S. PATENT DOCUMENTS

| | | |
|---|---|---|
| 4,545,390 | 10/1985 | Leary . |
| 4,790,331 | 12/1988 | Okada et al. ............................ 128/772 |
| 4,884,579 | 12/1989 | Engelson . |
| 4,955,862 | 9/1990 | Sepetka . |
| 4,968,306 | 11/1990 | Huss et al. .............................. 604/264 |
| 4,989,608 | 2/1991 | Ratner . |
| 4,994,069 | 2/1991 | Ritchart et al. . |
| 5,040,543 | 8/1991 | Badera et al. ........................... 128/772 |
| 5,050,606 | 9/1991 | Tremulis ................................. 128/673 |
| 5,095,915 | 3/1992 | Engelson . |
| 5,267,982 | 12/1993 | Sylvanowicz ............................ 604/281 |
| 5,306,252 | 4/1994 | Yutori et al. . |
| 5,376,084 | 12/1994 | Bacich et al. . |
| 5,437,288 | 8/1995 | Schwartz et al. . |
| 5,438,993 | 8/1995 | Lynch et al. . |
| 5,439,000 | 8/1995 | Gunderson et al. . |
| 5,441,483 | 8/1995 | Avitall . |
| 5,441,489 | 8/1995 | Utsumi et al. . |
| 5,460,187 | 10/1995 | Daigle et al. . |
| 5,477,856 | 12/1995 | Lundquist . |
| 5,520,645 | 5/1996 | Imran et al. . |
| 5,533,985 | 7/1996 | Wang ...................................... 604/264 |
| 5,573,520 | 11/1996 | Schwartz et al. ....................... 600/585 |

FOREIGN PATENT DOCUMENTS

PCT/US92/
07619 9/1992 WIPO .

*Primary Examiner*—Cary O'Connor
*Assistant Examiner*—Pamela L. Wingood
*Attorney, Agent, or Firm*—Thorpe, North & Western, LLP

[57] ABSTRACT

A hybrid tubular wire includes first and second elongate tubular bodies, fitted end to end, and about which a catheter may be threaded for guidance to a target location in a vasculature passageway of a body. The first elongate body has greater rotational stiffness than the second elongate body, which has greater lateral flexibility. Cuts are formed either by saw-cutting, laser cutting or etching at spaced-apart locations along the length of the second elongate body to increase its lateral flexibility. At least some of the cuts extend through the tubular body to the interior cavity to allow the escape of fluids flowing in the cavity.

24 Claims, 1 Drawing Sheet

HYBRID TUBULAR GUIDE WIRE FOR CATHETERS

BACKGROUND OF THE INVENTION

This invention relates to catheter systems and more particularly to a hybrid tubular guide wire apparatus with improved torque and flexure characteristics.

Catheter guide wires have been used for many years to "lead" or "guide" catheters to desired target locations in the human body's vasculature. The typical guide wire is from about 135 centimeters to 195 centimeters in length, and is made from two primary pieces—a stainless steel solid core wire, and a platinum alloy coil spring. The core wire is tapered on the distal end to increase its flexibility. The coil spring is typically soldered to the core wire at its distal end and at a point where the inside diameter of the coil spring matches the outside diameter of the core wire. Platinum is selected for the coil spring because it provides radiopacity for X-ray viewing during navigation of the guide wire in the body, and it is biocompatible. The coil spring also provides softness for the tip of the guide wire to reduce the likelihood of puncture of the anatomy.

Navigation through the anatomy is achieved by viewing the guide wire in the body using X-ray fluoroscopy. The guide wire is inserted into a catheter so the guide wire protrudes out the end, and then the wire and catheter are inserted into a vessel or duct and moved therethrough until the guide wire tip reaches a desired vessel or duct branch. The proximal end of the guide wire is then rotated or torqued to point the curved tip into the desired branch and then advanced farther. The catheter is advanced over the guide wire to follow or track the wire to the desired location, and provide additional support for the wire. Once the catheter is in place, the guide wire may be withdrawn, depending upon the therapy to be performed. Oftentimes, such as in the case of balloon angioplasty, the guide wire is left in place during the procedure and may be used to exchange catheters.

As the guide wire is advanced into the anatomy, internal resistance from the typically numerous turns, and surface contact, decreases the ability to advance the guide wire farther. This, in turn, may lead to a more difficult and prolonged procedure, or, more seriously, failure to access the desired anatomy and thus a failed procedure. A guide wire with both flexibility and good torque characteristics (torsional stiffness) would, of course, help overcome problems created by the internal resistance.

SUMMARY OF THE INVENTION

It is an object of the invention to provide an improved catheter guide wire apparatus.

It is also an object of the invention to provide such apparatus which exhibits both torsional stiffness, bending flexibility, and longitudinal strength.

It is a further object of the invention to provide such apparatus which is simple in design and construction.

The above and other objects of the invention are realized in a specific illustrative embodiment of a tubular catheter guide wire is formed of a first thin, elongate, hollow tubular body of first material, and a second thin, elongate, hollow tubular body of second material joined co-linearly to the first body. The first material has greater torsional stiffness and less lateral flexibility than the second material, but the tubular construction still provides significant torsional stiffness for the second body. With this embodiment, the guide wire, being hollow, may serve also as a catheter itself.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
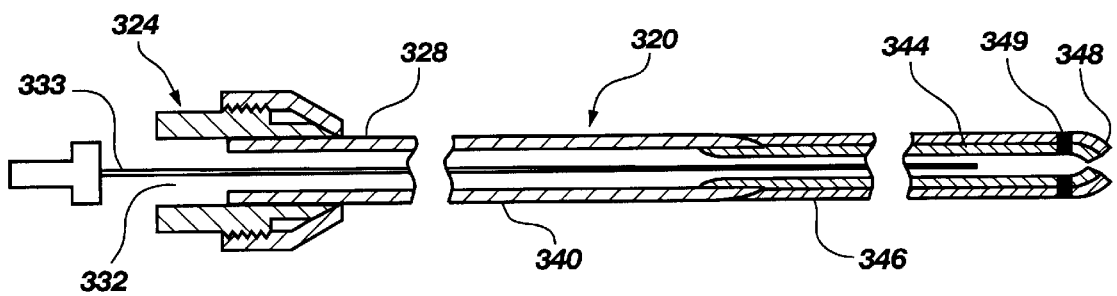
FIG. 1 is a side, fragmented, partially cross-sectional view of a hybrid tubular guide wire, in accordance with the present invention.

FIG. 1 is a side, fragmented, partially cross-sectional view of a hybrid tubular guide wire 320 made in accordance with the present invention. A pin vise type torquing chuck 324 is shown attached to a proximal end 328 in the usual manner. The chuck 324 also includes an opening, bore, or luer adapter 332 to allow for introduction of medications or other agents into the interior of the tubular guide wire 320. (The chuck 324 could be positioned farther toward the distal end, and would also be separate from the luer adapter.)

The hybrid tubular guide wire 320 is constructed of two sections 340 and 344, where section 344 has a smaller exterior diameter than section 340 and is inserted into and attached by adhesive or other fastening mechanism in the distal end of section 340. A lubricious tubular sleeve 346 may be installed over the section 344 to abut against the distal end of the section 340 to present a substantially smooth joint. Alternatively, a lubricious coating, film or layer could be applied to the exterior of section 340 and 344, as desired.

Insertable in the hollow of the tubular guide wire 320 is a tapered wire mandrel 333 which may be made radiopaque to X-ray fluoroscopy or, if magnetic resonance imaging (MRI) were used, the wire mandrel 333 could be made of a material active for MRI detection such as gadolinium or gadolinium compound, gadolinium encapsulated in a sheath, dysprosium, dysprosium compound or dysprosium encapsulated in a sheath. Alternatively, a radiopaque solution could be introduced into the interior of the tubular guide wire 320 or a solution visible in MRI could be used, if MRI rather than X-ray fluoroscopy were utilized of course, the guide wire 320 could be radiopaque or MRI detectable, and an appropriate solution could be introduced into the guide wire—to enhance visibility. The purpose of such a wire mandrel or solutions, of course, would be to allow tracking location and/or movement of the guide wire 320 as it is threaded into vasculature or body cavities.

The wire mandrel 333 could also be used to change the curvature of the tubular guide wire 320 as desired by the user. For example, the tubular guide wire 320 could be formed with a portion of it curved or angled and a straight wire mandrel 333 could then be inserted into the guide wire to straighten it out, and then removed when desired to allow the guide wire to resume the curved shape. Alternatively, the tubular guide wire 320 could be formed to be straight and the wire mandrel 333 formed with selected curves so that when the mandrel were inserted into the tubular guide wire, the mandrel would cause the guide wire to assume those same curves and when the mandrel were removed or the guide wire advanced beyond the curved portion of the mandrel, the guide wire tip would again straighten. In this manner, depending upon the initial shape of the wire mandrel 333 and/or the tubular guide wire 320, the shape of the guide wire can be controlled to a certain extent while disposed in vasculature or body cavities.

The wire mandrel 333 can also be used to change the flexibility of the guide wire 320—changing the taper or diameter of the mandrel 333 can provide for different degrees of stiffness of the guide wire.

Advantageously, section 340 of the tubular guide wire 320 is constructed of stainless steel and section 344 of nickel-titanium alloy. The section 340 of the tubular guide wire 320 could also be made of polymers or other flexible materials having suitable strength. The sleeve 346 could be made of a lubricious polymer such as polyethylene or a coated urethane.

Advantageously, the exterior diameter of section 340 could be 0.018 inches (or 0.036 inches), the interior diameter 0.012 inches (or 0.030 inches), while the exterior diameter of section 344 could advantageously be about 0.014 inches (or 0.032 inches). The interior hollow of the distal end of section 340 is bored to allow for snugly receiving and holding the proximal end of section 344. Glue or other adhesive might also be used to maintain the co-linear, telescopically fixed attachment. Advantageously, the length of section 344 could be about 35 cm, with the length of section 340 making up the rest of the standard length of a guide wire. The sleeve 346 advantageously is selected to have a thickness such that when installed on section 344, the diameter of that combination is substantially the same as the diameter of section 340 so that a smooth, unbroken guide wire length is presented.

Cuts, slots, gaps or openings may be formed in section 344 of the tubular guide wire 320 along the length thereof, either by saw cutting (e.g. diamond grit embedded semiconductor dicing blade); electron discharge machining, laser cutting or etching (for example using the etching process described in U.S. Pat. No. 5,106,455) anisotropically to provide for lateral flexibility in section 344. The cuts would generally be perpendicular or crosswise to the long dimension of the guide wire and placed on alternate sides of the guide wire. However, the cuts could also be angled to allow for a longer cut. Controlling and varying both the spacing and depth of the cuts allows for selection of the flexure profile of the tubular guide wire, the more closely spaced the cuts and the greater depth thereof giving rise to a more flexible guide wire, and vice-versa.

The distal end 348 of the guide wire advantageously is rounded to minimize the chance of traumatic piercing of body tissue. Also formed on the distal end 340 may be a radiopaque or MRI marker or band 349. The band 349 may be gold or platinum alloy (for X-ray fluoroscopy) or gadolinium or dysprosium, or compounds thereof (for MRI), and may be formed on the distal end 340 by deposition, wrapping or use of the shape memory alloy (NiTi) effect to "lock" the band around the end. Alternatively, a radiopaque plug may be disposed in the lumen at the distal end 340 (or an MRI marker).

Figure 2:
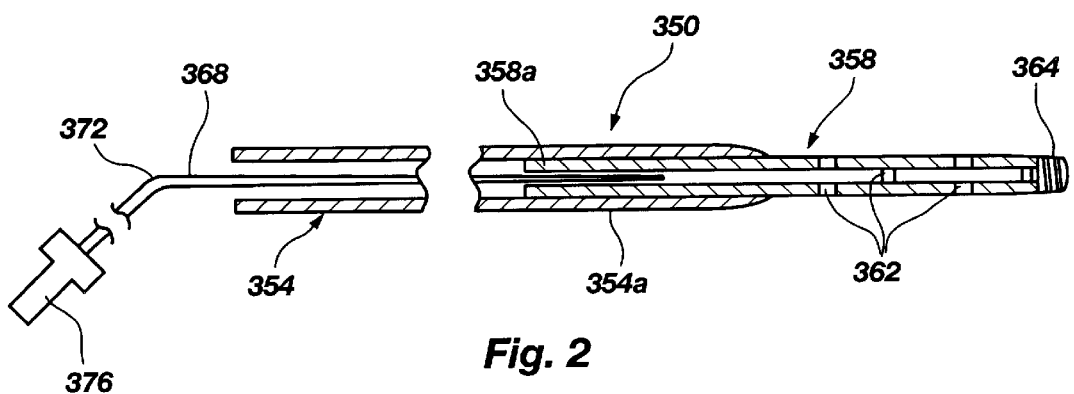
FIG. 2 shows a side, fragmented, partially cross-sectional view of another embodiment of a hybrid tubular guide wire, in accordance with the present invention.

FIG. 2 is a side, fragmented view of an alternative embodiment of a hybrid tubular guide wire 350 made in accordance with the present invention. The guide wire 350, as with the guide wire of FIG. 1, is composed of two sections 354 and 358. Section 354 is advantageously made of stainless steel and is dimensioned to receive in the hollow of its distal end 354a, the proximal end 358a of section 358. Advantageously, section 358 is made of nickel-titanium alloy to achieve greater lateral flexibility than section 354. The distal end 354a of section 354 is tapered on its exterior surface to present a gradual joint between section 354 and section 358, to avoid damaging vasculature passageway walls into which it may be inserted. Section 358 could be held in place in the hollow of section 354 by press fitting, a suitable adhesive, and/or using the shape memory effect.

Cuts 362 are shown formed in section 358 at spaced apart locations and on the top, bottom and sides of the section, to increase the section's lateral flexibility, while maintaining a desirable level of torsional stiffness. A plug 364, which may be made of a radiopaque material or an MRI sensitive material, or both, is disposed in the distal end of section 358 to provide enhanced visibility of the guide wire, and is rounded to reduce trauma and likelihood of damage of vasculature passageways. The radiopacity or MRI sensitivity, of course, allows for tracking the movement and/or visualizing of the guide wire 350 in the vasculature.

Shown disposed in the hollow of the guide wire 350 is a wire mandrel 368 having a bend 372 such that when inserted into the guide wire 350 would cause the guide wire to assume the same bend shape, and when removed, would result in the guide wire straightening again. The bend 372 would generally be quite distal in the mandrel. A stop 376 is attached to the proximal end of the mandrel 368 to prevent insertion of the mandrel beyond a certain point in the guide wire. The stop might also simply be a section of hypotube disposed over the proximal end of the mandrel.

Figure 3:
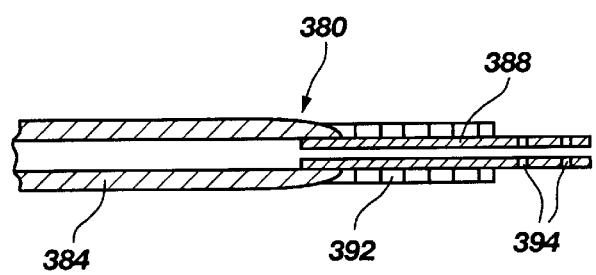
FIG. 3 shows a side, fragmented, partially cross-sectional view of still another embodiment of a hybrid tubular guide wire, in accordance with the present invention.

FIG. 3 is a side, fragmented view of another embodiment of a hybrid tubular guide wire 380 made in accordance with the present invention. The guide wire 380, as with the other guide wires, is composed of two sections 384 and 388, with section 388 fitted at its proximal end in the distal end of section 384. A sleeve 392 is fitted over a portion of section 388 but leaving the distal end of section 388 to protrude therefrom. Cuts 394 are formed in the distal end of section 388 to allow for the lateral escape of solutions introduced into the proximal end of section 384 (as well as for flexibility, etc.), as discussed for the embodiment of FIG. 2. In this case, the end of section 388 is flexible to serve as a guide wire in the desired fashion. Section 384 might illustratively be made of stainless steel and section 388 of nickel-titanium alloy. The sleeve 392 would be made of a lubricious material.

With the hybrid tubular guide wire of the present invention, significant torsional stiffness can be achieved with the stainless steel sections and then by inclusion of the nickel-titanium alloy distal section, great lateral flexibility can be achieved to allow threading of the guide wire into vasculature passageways. Because the nickel-titanium alloy sections are tubular in construction, and are micro machined, reasonable rotational stiffness is still achieved. Thus, both rotational stiffness and lateral flexibility at the leading or distal end of the guide wire are made possible.

The hybrid tubular guide wire disclosed can be used with a catheter threaded thereover in a conventional manner, or can be used to deliver medication to a target location in a manner similar to the catheters themselves. With cuts formed along at least a portion of the length of the tubular guide wires, the medication is allowed to leak from the bore of the guide wire out into the vasculature passageway. Of course, the location of discharge of medication from the tubular guide wire can be controlled by controlling depth of the cuts as well as the location thereof. In addition, a polymer sleeve may be inserted in the lumen or bore of a tubular guide wire, and/or on the outside as well, for sealing and preventing the outflow or discharge of medication from the guide wire lumen. Controlling the length of such sleeves on the guide wire enables control of discharge points of medication from the guide wire. Also, cuts could be formed in the sleeves to provide other discharge points.

In addition, a stiffening mandrel or wire can be inserted through the bore or lumen of a tubular guide wire as already discussed, and such mandrel or wire can be curved at selected locations such as location 372 in the mandrel 368 of FIG. 2, to cause a corresponding bend in the tubular guide wire. Alternatively, the tubular guide wire can be formed with one or more bends and then a substantially straight mandrel may be inserted into the hollow of the guide wire to cause it to straighten as needed. Also, the mandrel can be made of a material so that it is visible either with X-ray fluoroscopy or MRI, depending upon the process used to view the clinical procedure.

In the embodiments of the guide wire discussed above, the guide wires can be made "flow directable" by providing highly flexible distal ends. "Flow directability" means that the distal end of the guide wire tends to "flow" with the blood around curves and bends in a vasculature passageway. To reduce resistance to movement of a guide wire in a vasculature passageway, the surface of the guide wire may be electropolished, sandblasted (with sand, glass beads, sodium bicarbonate, etc.) or otherwise treated, to increase the smoothness thereof, and additionally, a lubricious coating may be applied to the surface of the guide wire—such coatings might illustratively include silicone based oil and/ or polymer or hydrophilic polymers. Alternatively, a lubricous sleeve made, for example, of a hydrophilic polymer could also be provided for disposal about the guide wire.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A hybrid tubular guide wire for introduction into a vessel or duct pathway to guide a catheter, if desired, to a predetermined location, comprising a first thin elongate hollow tubular section having tubular walls defining a lumen, and made of a material having a predetermined torsional stiffness and lateral flexibility, and a second thin elongate hollow tubular section having less torsional stiffness and greater lateral flexibility than the first section, said second section attached co-linearly to the first section.

2. A guide wire as in claim 1 wherein the exterior surface of the second section includes a plurality of cuts spaced apart along at least a portion of the length of the second section, to increase lateral flexibility thereof.

3. A guide wire as in claim 1 wherein the second section has a proximal end and distal end, and wherein the guide wire further includes a radiopaque element disposed at the distal end of the second section.

4. A guide wire as in claim 1 wherein the second section has a proximal end and a distal end, and wherein the guide wire further includes an MRI detectable element disposed at the distal end of the second section.

5. A guide wire as in claim 1 wherein the first and second sections are dimensioned to enable inserting one end of the second section into the lumen of the first section, to secure the second section therein.

6. A guide wire as in claim 5, wherein the outside diameter of the first tubular section is from about 0.010 to 0.038 inches, the diameter of the lumen is from about 0.006 to 0.030 inches, and the outside diameter of the second section is from about 0.008 to 0.032.

7. A guide wire as in claim 6, wherein the outside diameter of the first tubular section is about 0.018 inches, wherein the diameter of the lumen is 0.012 inches, and wherein the outside diameter of the second section is about 0.014 inches.

8. A guide wire as in claim 1 wherein the first section is made of stainless steel and wherein the second section is made of nickel-titanium alloy.

9. A guide wire as in claim 1 further including an elongate wire disposable in the lumen of the first section and hollow of the second section and slidable therein to selectively stiffen that portion of the lengths of the sections occupied by the wire.

10. A guide wire as in claim 9, wherein said elongate wire includes a stop means formed therein for preventing insertion of the wire in the lumen and hollow beyond a certain point.

11. A guide wire as in claim 9, wherein said elongate wire includes one or more bends so that when it is disposed in the lumen and hollow of the sections, the sections bend to conform to the bend in the elongate wire.

12. A guide wire as in claim 9, wherein the elongate sections are preshaped with one or more bends, and wherein the elongate wire is preshaped to be substantially straight such that when the elongate wire is disposed in the lumen and hollow of the sections at the location of a bend, the elongate wire causes the sections to substantially straighten.

13. A guide wire as in claim 9, wherein the elongate wire is made of a radiopaque material.

14. A guide wire as in claim 9, wherein the elongate wire is made of a material detectable by MRI.

15. A guide wire as in claim 9, wherein the elongate wire is tapered at least along a portion thereof, with the distal end being narrower than the proximal end.

16. A guide wire as in claim 1 further including a tubular sleeve for slidable disposition over the second section to abut the end of the first section, so that the exterior diameters of the first section and tubular sleeve are substantially the same.

17. A guide wire as in claim 16, wherein the tubular sleeve is made of a material selected from the group consisting of elastomers, polyurethane, polyethylene, and teflon.

18. A guide wire as in claim 16, wherein the tubular sleeve and second section are generally coterminous.

19. A guide wire as in claim 16, wherein the second section protrudes out the distal end of the tubular sleeve.

20. A guide wire as in claim 16, wherein the tubular sleeve is coated with a lubricious material.

21. A combination catheter/catheter guide wire comprising a first elongate hollow tubular body formed of stainless steel, and having tubular sidewalls defining a central lumen, a second elongate hollow tubular body formed of nickel-titanium alloy, and having tubular sidewalls defining a central lumen and having greater lateral flexibility than the first tubular body, said second tubular body being joined end to end with the first tubular body, said sidewalls of the second tubular body having slots formed therein along the length thereof to increase the lateral flexibility of the body, at least some of said slots extending through the sidewalls to the lumen to allow discharge therethrough of fluids flowing in the lumen.

22. A catheter/catheter guide wire as in claim 21, wherein said second tubular body is fitted at a proximal end into the lumen of the first tubular body at a distal end.

23. A catheter/catheter guide wire as in claim 21, further including a plug disposed in the distal end of the second tubular body, said plug being made of a material selected from the group consisting of radiopaque material and MRI detectable material.

24. A combination catheter/catheter guide wire comprising a first elongate hollow tubular body having tubular sidewalls defining a central lumen, a second elongate hollow tubular body having tubular sidewalls defining a central lumen and having greater lateral flexibility than the first tubular body, said second tubular body being joined end to end with the first tubular body, said sidewalls of the second tubular body having slots formed therein along the length thereof to increase the lateral flexibility of the body, at least some of said slots extending through the sidewalls to the lumen to allow discharge there through of fluids flowing in the lumen, said second tubular body further comprising a plug disposed in the distal end thereof, said plug being made of a material selected from the group consisting of radiopaque material and MRI detectable material.

* * * * *